United States Patent
Cowley

(10) Patent No.: US 10,828,020 B2
(45) Date of Patent: Nov. 10, 2020

(54) SURGICAL RETRACTOR INCLUDING THREE-DIMENSIONAL (3D) IMAGING CAPABILITY

(71) Applicant: COVIDIEN LP, Mansfield, MA (US)

(72) Inventor: Matthew S. Cowley, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 24 days.

(21) Appl. No.: 16/108,292

(22) Filed: Aug. 22, 2018

(65) Prior Publication Data

US 2020/0060669 A1 Feb. 27, 2020

(51) Int. Cl.
| | |
|---|---|
| *A61B 17/02* | (2006.01) |
| *A61B 90/00* | (2016.01) |
| *A61B 8/08* | (2006.01) |
| *A61B 17/00* | (2006.01) |
| *A61B 18/00* | (2006.01) |

(52) U.S. Cl.
CPC .......... *A61B 17/0218* (2013.01); *A61B 8/085* (2013.01); *A61B 90/37* (2016.02); *A61B 2017/00106* (2013.01); *A61B 2017/00221* (2013.01); *A61B 2018/00577* (2013.01); *A61B 2090/378* (2016.02)

(58) Field of Classification Search
CPC ..... A61B 17/0218; A61B 8/085; A61B 90/37; A61B 2090/3788; A61B 2090/3786; A61B 2090/3784; A61B 2090/3782; A61B 2090/378
See application file for complete search history.

(56) References Cited

U.S. PATENT DOCUMENTS

| | | | |
|---|---|---|---|
| 5,413,107 | A | 5/1995 | Oakley et al. |
| 6,626,855 | B1 * | 9/2003 | Weng ........................ A61B 8/12 600/439 |
| 6,692,450 | B1 | 2/2004 | Coleman |
| 6,719,694 | B2 | 4/2004 | Weng et al. |
| 7,615,015 | B2 | 11/2009 | Coleman |
| 8,152,721 | B2 | 4/2012 | Michaeli et al. |
| 8,480,585 | B2 | 7/2013 | Slayton et al. |
| 9,220,478 | B2 | 12/2015 | Smith et al. |
| 2004/0158153 | A1 * | 8/2004 | Hirt ........................ A61B 8/12 600/443 |
| 2007/0073135 | A1 | 3/2007 | Lee et al. |
| 2009/0012394 | A1 * | 1/2009 | Hobelsberger ........... A61B 8/13 600/437 |
| 2009/0076390 | A1 | 3/2009 | Lee et al. |
| 2012/0302877 | A1 | 11/2012 | Harks et al. |

(Continued)

*Primary Examiner* — Christopher J Beccia
(74) *Attorney, Agent, or Firm* — Carter, DeLuca & Farrell LLP

(57) ABSTRACT

A surgical retractor includes a shaft and an end effector extending distally from the shaft. The end effector includes a distal finger extending about at least a portion of a perimeter of a geometric shape and configured to facilitate retraction of tissue. The end effector further includes an ultrasound sensor array including a plurality of ultrasound sensors disposed in spaced-apart relation along the distal finger. Each ultrasound sensor of the plurality of ultrasound sensors is configured to emit an ultrasound wave and receive an echoed wave. The echoed waves received by the plurality of ultrasound sensors are output to be reconstructed to produce a real-time 3D ultrasound video image.

13 Claims, 2 Drawing Sheets

(56) References Cited

U.S. PATENT DOCUMENTS

2014/0133269 A1    5/2014  Hansen
2015/0257779 A1    9/2015  Sinelnikov et al.
2016/0183910 A1*  6/2016  Tahmasebi Maraghoosh ............ A61B 8/085
                                                  600/462

* cited by examiner

# SURGICAL RETRACTOR INCLUDING THREE-DIMENSIONAL (3D) IMAGING CAPABILITY

BACKGROUND

Technical Field

The present disclosure relates generally to surgical instrumentation. More specifically, the present disclosure relates to a surgical retractor including three-dimensional (3D) imaging capability to facilitate surgical procedures.

Background of Related Art

Liver tumors are relatively common occurrences and, as a result, surgical procedures involving the treatment or removal of liver tumors are also relatively common. Despite being relatively common, minimally-invasive surgical procedures to treat or remove liver tumors remain difficult, particular with respect to accurately locating the liver tumor. As a result, larger-than-necessary tracts of liver tissue are treated (e.g., ablated) or removed (e.g., resected) to ensure that the entire tumor is treated or removed.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein.

Provided in accordance with aspects of the present disclosure is a surgical retractor including a shaft and an end effector. The end effector extends distally from the shaft and includes a distal finger extending about at least a portion of a perimeter of a geometric shape and configured to facilitate retraction of tissue. The end effector further includes an ultrasound sensor array including a plurality of ultrasound sensors disposed in spaced-apart relation along the distal finger. Each ultrasound sensor of the plurality of ultrasound sensors is configured to emit an ultrasound wave and receive an echoed wave, wherein the echoed waves received by the plurality of ultrasound sensors are output to be reconstructed to produce a real-time 3D ultrasound video image.

In an aspect of the present disclosure, an articulation joint interconnects the shaft and the end effector to enable articulation of the end effector about at least one axis relative to the shaft. In aspects, the end effector is articulatable about at least two axes relative to the shaft.

In another aspect of the present disclosure, the distal finger extends about at least a portion of a perimeter of an arcuate geometric shape. In aspects, the distal finger extends about at least portion of a circumference of a circle.

In yet another aspect of the present disclosure, at least one pair of two ultrasound sensors of the plurality of ultrasound sensors oppose one another.

In still another aspect of the present disclosure, the distal finger extends about at least 50% of the perimeter of the geometric shape.

A surgical system provided in accordance with aspects of the present disclosure includes a surgical retractor and a control system. The surgical retractor includes a shaft and an end effector extending distally from the shaft. The end effector includes a distal finger extending about at least a portion of a perimeter of a geometric shape and configured to facilitate retraction of tissue. The end effector further includes an ultrasound sensor array including a plurality of ultrasound sensors disposed in spaced-apart relation along the distal finger. Each ultrasound sensor of the plurality of ultrasound sensors is configured to emit an ultrasound wave and receive an echoed wave. The control system is configured to receive the echoed waves from the plurality of ultrasound sensors and reconstruct the echoed waves to produce a real-time 3D ultrasound video image.

In an aspect of the present disclosure, the control system further includes a visual display configured to display the real-time 3D ultrasound video image.

In another aspect of the present disclosure, the surgical retractor further includes an articulation joint interconnecting the shaft and the end effector. The end effector is articulatable about at least one axis or, in embodiments, about at least two axes, relative to the shaft.

In still another aspect of the present disclosure, the distal finger extends about at least a portion of a perimeter of an arcuate geometric shape. In aspects, the distal finger extends about at least portion of a circumference of a circle.

In yet another aspect of the present disclosure, at least one pair of two ultrasound sensors of the plurality of ultrasound sensors oppose one another.

In still yet another aspect of the present disclosure, the distal finger extends about at least 50% of the perimeter of the geometric shape.

A method of surgery provided in accordance with aspects of the present disclosure includes inserting an end effector of a surgical retractor into an internal surgical site, manipulating the end effector to retract tissue, positioning the end effector on tissue of interest, activating an ultrasound sensor array on the end effector to produce a real-time 3D ultrasound video image, and viewing the real-time 3D ultrasound video image on a visual display.

In an aspect of the present disclosure, manipulating the end effector includes articulating the end effector of the surgical retractor relative to a shaft of the surgical retractor.

In another aspect of the present disclosure, the method further includes moving the end effector along the tissue of interest and continuing to view the real-time 3D ultrasound video image on the visual display.

In yet another aspect of the present disclosure, the method further comprises determining a location of a tumor based on the viewing of the real-time 3D ultrasound video image on the visual display. In still another aspect of the present disclosure, the method further includes treating or removing the tumor.

BRIEF DESCRIPTION OF THE DRAWINGS

Various aspects and features of the present disclosure are described herein with reference to the drawings, wherein like reference numerals identify similar or identical components, and.

DETAILED DESCRIPTION

Figure 1:
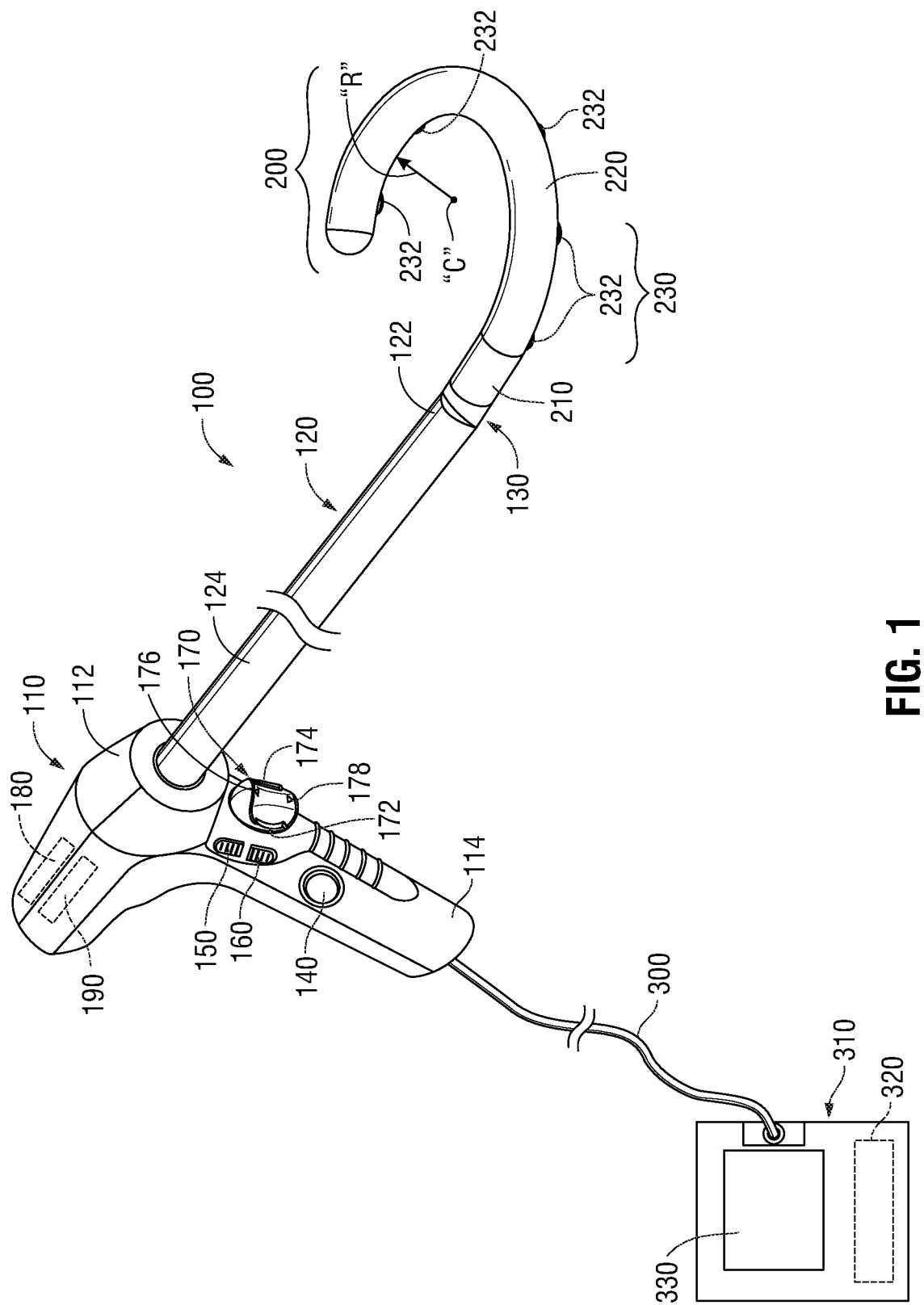
FIG. 1 is a top, front, perspective view of a surgical retractor provided in accordance with aspects of the present disclosure.

Turning to FIG. 1, provided in accordance with the present disclosure is a surgical retractor including three-dimensional (3D) imaging capability to facilitate performing a surgical procedure such as, for example, by facilitating retraction of tissue and/or accurately locating tissue structures, e.g., a tumor. The surgical retractor, generally identified by reference numeral 100, is detailed herein for use in connection with hepatic surgical procedures performed on the liver; however, the aspects and features of the present disclosure are equally applicable for use in other surgical procedures and/or with respect to other tissue structures.

Continuing with reference to FIG. 1, surgical retractor 100 generally includes a housing 110, a shaft 120 extending distally from housing 110, and an end effector 200 extending distally from shaft 120. Surgical retractor 100 is further configured, in embodiments, to enable articulation of end effector 200 relative to shaft 120 and, thus, in such embodiments, includes one or more articulation joints 130 disposed between and interconnecting a distal end portion 122 of shaft 120 with end effector 200. Articulation joint(s) 130 enables articulation of end effector 200 relative to shaft 120, thus facilitating the insertion of surgical retractor 100 through a minimally-invasive access port (not shown), e.g., a trocar, and/or manipulation of end effector 200 within a minimally-invasive surgical site to facilitate imaging of a desired area within the minimally-invasive surgical site.

Housing 110 of surgical retractor 100 defines a pistol-grip configuration (although other configurations are also contemplated) including a barrel portion 112 and a fixed handle portion 114 depending from barrel portion 112. Shaft 120 extends distally from barrel portion 112, while fixed handle portion 114 is ergonomically configured to facilitate a user gripping and manipulating housing 110. A cable 300 couples housing 110 to a control system 310. Control system 310 provides power to surgical retractor 100, although power may alternatively be provided by a battery (not shown) internal to housing 110 or via a separate cable (not shown) connected directly to a mains power supply (not shown). Control system 310 also includes an image processing unit 320 and a visual display 330. Although illustrated as incorporated into a single enclosure, control system 310 may include separate components connected to one another such as, for example, a computer for image processing and a video monitor connected to the computer for visual display. In other embodiments, imaging processing and/or image display may be provided on or within housing 110. Additionally or alternatively, wireless communication to local or remote components, e.g., a computer and/or display, may be provided instead of a wired connection using cable 300.

Housing 110 of surgical retractor 100 further includes a plurality of actuators 140-170 such as, for example, an ON/OFF imaging button 140, a clockwise rotation button 150, a counterclockwise rotation button 160, and an articulation joystick 170 including first and second yaw articulation buttons 172, 174, respectively, and first and second pitch articulation buttons 176, 178, respectively. ON/OFF imaging button 140 enables selective activation and deactivation of 3D ultrasound imaging by end effector 200; clockwise and counterclockwise rotation buttons 150, 160 enable respective clockwise and counterclockwise rotation of shaft 120 and/or end effector 200 relative to housing 110; and articulation joystick 170 enables pitch and yaw articulation of end effector 200 relative to shaft 120 about articulation joint 130.

Clockwise and counterclockwise rotation buttons 150, 160 communicate with a powered rotation mechanism 180 including one or more motors operably coupled to shaft 120 such that, upon actuation of either of buttons 150, 160, shaft 120 is rotated in the corresponding direction relative to housing 110 to thereby rotate end effector 200 with shaft 120 and relative to housing 110. Alternatively, powered rotation mechanism 180 may be operably coupled to end effector 200 with shaft 120 remaining rotationally fixed relative to housing 110. In such embodiments, buttons 150, 160 communicate with powered rotation mechanism 180 to rotate end effector 200 relative to shaft 120 and housing 110. As an alternative to powered rotation mechanism 180, a manual rotation mechanism including, for example, a manually-actuated rotation wheel (not shown), may be provided. In embodiments, rotation is omitted entirely.

Articulation joystick 170 communicates with a powered articulation mechanism 190 including one or more motors operably coupled with shaft 120, articulation joint 130, and end effector 200 via one or more translation drives, rotation drives, cables, linkages, tilt plates, etc. to articulate end effector 200 about articulation joint 130 and relative to shaft 120 in the corresponding direction according to the button actuated, e.g., yaw articulation button 172, yaw articulation button 174, pitch articulation button 176, or pitch articulation button 178. As an alternative to powered articulation mechanism 190, a manual articulation mechanism including, for example, one or more manually-actuated articulation wheels (not shown), may be provided. In either configuration, articulation joint 130 provides articulation of end effector 200 relative to shaft 120 about two axes (a yaw axis and a pitch axis), although in some embodiments articulation about a single axis is provided.

Figure 2:
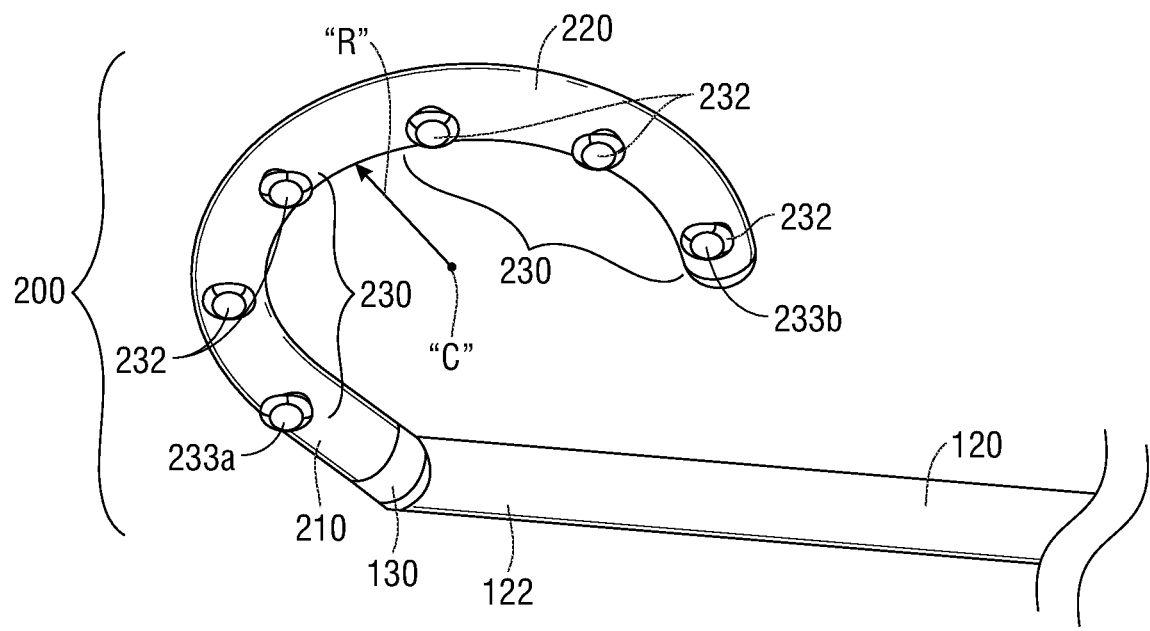
FIG. 2 is a bottom, front, perspective view of an end effector of the surgical retractor of FIG. 1.

Referring also to FIG. 2, as noted above, shaft 120 extends distally from housing 110 and end effector 200 extends distally from shaft 120 and is operably coupled to shaft 120 by way of articulation joint 130. A proximal end portion 124 of shaft 120, more specifically, is coupled to powered rotation mechanism 180 at or within housing 110. Shaft 120 extends distally from proximal end portion 124 to distal end portion 122. Distal end portion 122 is operably coupled with articulation joint 130, as also noted above.

End effector 200 includes a proximal arm 210 that is operably coupled with articulation joint 130 on an opposite side thereof relative to distal end portion 122 of shaft 120 such that proximal arm 210 of end effector 200 is articulatable relative to distal end portion 122 of shaft 120 about articulation joint 130, e.g., in response to actuation of articulation joystick 170. End effector 200 further includes a distal finger 220 fixed relative to and extending distally from proximal arm 210. Distal finger 220 defines an arcuate configuration and may include a radius of curvature "R" defined from a center "C." In embodiments, distal finger 220 extends about at least a portion of a circumference of a circle centered on center "C" and having radius of curvature "R." In embodiments, distal finger 220 extends about at least 50% of the circumference of that circle. As an alternative to defining a portion of a circumference of a circle, distal finger 220 may define a portion of a perimeter of an ellipse or other suitable arcuate geometric shape. Further still, instead of defining an arcuate configuration, distal finger 220 may include a plurality of angled segments so as to form a portion of a polygon, e.g., in embodiment, at least 50% of the outer perimeter of the polygon, centered about center "C." However, other configurations are also contemplated such as, for example, a configuration including one or more arcuate portions and one or more straight portions configurations, e.g., a partially-arcuate and partially-polygonal configuration.

With particular reference to FIG. 2, the above-detailed configuration of distal finger 220 enables distal finger 220 to be utilized to retract tissue to provide access to underlying tissue. Rotating and/or articulating end effector 200 also facilitate the use of distal finger 220 to retract tissue by enabling distal finger 200 to be properly positioned and oriented relative to tissue.

In addition to functioning as an articulating tissue retractor, distal finger 220 enables 3D ultrasound imaging of tissue. To this end, distal finger 220 includes a plurality of ultrasound sensors 232 disposed in spaced-apart relation along distal finger 220 to form an ultrasound sensor array 230. In embodiments where distal finger 220 extends about at least 50% of a circumference or perimeter at least one pair of ultrasound sensors 232 may be disposed at diametrically-opposed locations 233a, 233b. Although six (6) equally-spaced ultrasound sensors 232 are illustrated, other suitable number and/or configuration of ultrasound sensors 232 to achieve a desired ultrasound sensor array 230 may be provided. More specifically, any suitable configuration where ultrasound sensors 232 are appropriately spaced along distal finger 220 (whether distal finger 220 defines a portion of a circle, a portion of a polygon, a partially-polygonal, partially-arcuate configuration, etc.) to enable reconstruction of a 3D ultrasound image therefrom may be provided.

Each ultrasound sensor 232 in the ultrasound sensor array 230 is configured to emit ultrasound waves, e.g., high-frequency sound waves, and to receive echoed waves produced by the reflection of the ultrasound waves against the various tissue structures encountered. The echoed waves received by each ultrasound sensor 232 are output to the image processing unit 320 (FIG. 1), e.g., by way of wires (not shown) extending through surgical retractor 100 and cable 300 (see FIG. 1). Image processing unit 320 (FIG. 1) utilizes the data from each of the ultrasound sensors 232 to reconstruct a 3D image. 3D image reconstruction may be provided via any suitable method including, for example, voxel-Based Methods (VBMs), Pixel-Based Methods (PBMs), or Function-Based Methods (FBMs). Other suitable methods for producing a 3D image from an ultrasound sensor array, e.g., ultrasound sensor array 230, are also contemplated.

The above-detailed process is repeated in real-time such that a stream of 3D images are produced, thus providing a real-time 3D ultrasound video image. The real-time 3D ultrasound video image is output to visual display 330 (FIG. 1), enabling a user to visualize the internal tissue structures in real-time as end effector 200 is maneuvered within an internal surgical site.

Figure 3:
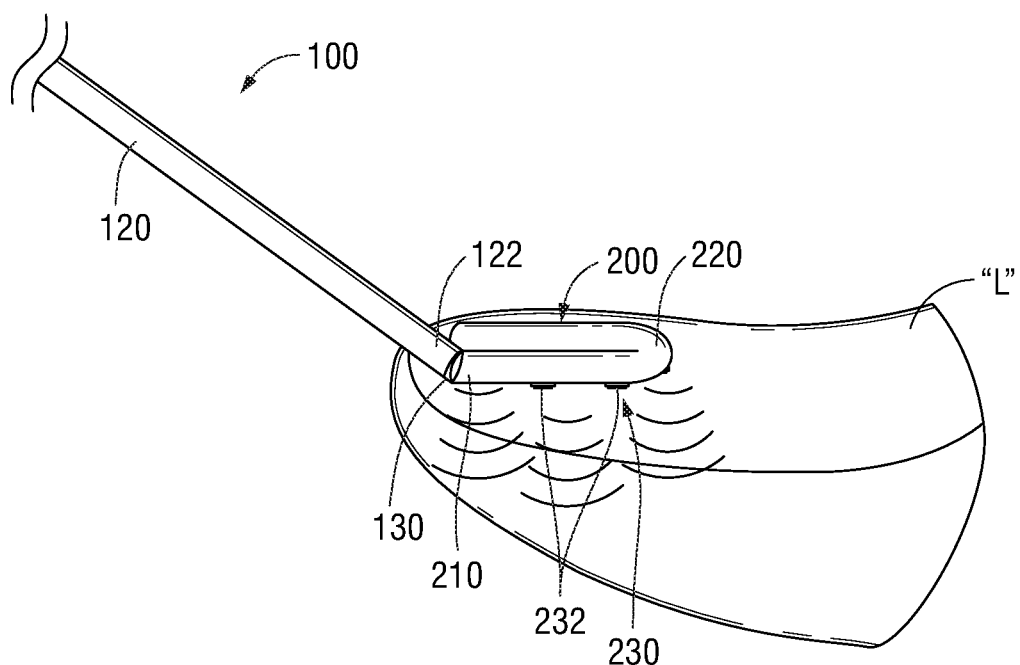
FIG. 3 is a side, perspective view illustrating a distal portion of the surgical retractor of FIG. 1 in use imaging liver tissue.

Referring to FIG. 3, in use, with respect to the liver "L," for example, end effector 200 is inserted through a minimally-invasive access port (not shown), e.g., a trocar, and is articulated, rotated, and/or otherwise maneuvered to retract tissue and reach the liver "L." 3D ultrasound imaging is then activated, e.g., by depressing ON/OFF imaging button 140 (FIG. 1), and distal finger 220 of end effector 200 is moved along the surface of the liver "L," thereby moving ultrasound sensor array 230 along the surface of the liver "L." The user may maneuver ultrasound sensor array 230 while watching the real-time 3D ultrasound video image displayed on visual display 330 (FIG. 1). This enables the user to accurately locate a tumor to be treated or removed. Once accurately located, the tumor may be marked or otherwise indicated, if required. The tumor may then be treated, e.g., ablated, or removed, e.g., resected. By accurately locating the tumor utilizing the 3D ultrasound imaging provided by end effector 200, as detailed above, only the necessary tissue is treated or removed and unaffected tissue is left undisturbed.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical retractor, comprising:
   a shaft; and
   an end effector extending distally from the shaft, the end effector including:
   a distal finger defining a fixed configuration, extending about at least a portion of a perimeter of a geometric shape, and configured to facilitate retraction of tissue; and
   an ultrasound sensor array including a plurality of ultrasound sensors disposed in spaced-apart relation along the distal finger, each ultrasound sensor of the plurality of ultrasound sensors configured to emit an ultrasound wave and receive an echoed wave, wherein the echoed waves received by the plurality of ultrasound sensors are output to be reconstructed to produce a real-time 3D ultrasound video image; and
   an articulation joint interconnecting the shaft and the end effector and configured to enable articulation of the end effector about at least one axis relative to the shaft.

2. The surgical retractor according to claim 1, wherein the end effector is articulable about at least two axes relative to the shaft.

3. The surgical retractor according to claim 1, wherein the distal finger extends about at least a portion of a perimeter of an arcuate geometric shape.

4. The surgical retractor according to claim 3, wherein the distal finger extends about at least portion of a circumference of a circle.

5. The surgical retractor according to claim 1, where at least one pair of two ultrasound sensors of the plurality of ultrasound sensors oppose one another.

6. The surgical retractor according to claim 1, wherein the distal finger extends about at least 50% of the perimeter of the geometric shape.

7. A surgical system, comprising:
   a surgical retractor including a shaft and an end effector extending distally from the shaft, the end effector including a distal finger defining a fixed configuration, extending about at least a portion of a perimeter of a geometric shape, and configured to facilitate retraction of tissue, the end effector further including an ultrasound sensor array including a plurality of ultrasound sensors disposed in spaced-apart relation along the distal finger, each ultrasound sensor of the plurality of ultrasound sensors configured to emit an ultrasound wave and receive an echoed wave; and a control system configured to receive the echoed waves from the plurality of ultrasound sensors and reconstruct the echoed waves to produce a real-time 3D ultrasound video image; and an articulation joint interconnecting the shaft and the end effector and configured to enable articulation of the end effector about at least one axis relative to the shaft.

8. The surgical system according to claim 7, wherein the control system further includes a visual display configured to display the real-time 3D ultrasound video image.

9. The surgical system according to claim 7, wherein the end effector is articulable about at least two axes relative to the shaft.

10. The surgical system according to claim 7, wherein the distal finger extends about at least a portion of a perimeter of an arcuate geometric shape.

11. The surgical system according to claim 10, wherein the distal finger extends about at least portion of a circumference of a circle.

12. The surgical system according to claim 7, where at least one pair of two ultrasound sensors of the plurality of ultrasound sensors oppose one another.

13. The surgical system according to claim 7, wherein the distal finger extends about at least 50% of the perimeter of the geometric shape.

* * * * *